(12) United States Patent
Verdooner

(10) Patent No.: US 9,854,963 B2
(45) Date of Patent: *Jan. 2, 2018

(54) APPARATUS AND METHOD FOR IDENTIFYING ONE OR MORE AMYLOID BETA PLAQUES IN A PLURALITY OF DISCRETE OCT RETINAL LAYERS

(75) Inventor: Steven Roger Verdooner, Sacramento, CA (US)

(73) Assignee: NeuroVision Imaging LLC, Sacramento, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/433,139

(22) Filed: Mar. 28, 2012

(65) Prior Publication Data

US 2012/0251452 A1    Oct. 4, 2012

Related U.S. Application Data

(60) Provisional application No. 61/468,818, filed on Mar. 29, 2011.

(51) Int. Cl.
| | |
|---|---|
| A61B 3/00 | (2006.01) |
| A61B 3/14 | (2006.01) |
| A61B 3/10 | (2006.01) |
| A61B 5/00 | (2006.01) |
| A61K 49/00 | (2006.01) |

(52) U.S. Cl.
CPC ............ *A61B 3/102* (2013.01); *A61B 5/0066* (2013.01); *A61B 5/0071* (2013.01); *A61K 49/0021* (2013.01); *A61B 2576/026* (2013.01)

(58) Field of Classification Search
USPC .................................................. 351/200–246
See application file for complete search history.

(56) References Cited

U.S. PATENT DOCUMENTS

| | | |
|---|---|---|
| 7,575,321 B2 | 8/2009 | Newman |
| 2009/0304591 A1 | 12/2009 | Russmann |

OTHER PUBLICATIONS

Perez et al., beta-Amyloid Deposition and Functional Impairment in the Retina of the APPswe/PS1deltaE9 Transgenic Mouse Model of Alzheimer's Disease. Investigative Ophthalmology & Visual Science, Feb. 2009, vol. 50, No. 2, 793-800.*
Ning et al., Amyloid-beta Deposits Lead to Retinal Degeneration in a Mouse Model of Alzheimer Disease. Investigative Ophthalmology & Visual Science, Nov. 2008, vol. 49, No. 11, 5136-5143.*
Spaide et al., Drusen Characterization with Multimodal Imaging. Retina. Oct. 2010 ; 30(9): 1441-1454.*
Ryu et al., Curcumin and Dehydrozingerone Derivatives: Synthesis, Radiolabeling, and Evaluation for beta-Amyloid Plaque Imaging. J. Med. Chem. 2006, 49, 6111-6119.*
U.S. Appl. No. 13/280,161, filed Oct. 2011, Verdooner.*
U.S. Appl. No. 13/053,934, filed Mar. 2011, Verdooner.*

(Continued)

*Primary Examiner* — Mohammed Hasan
(74) *Attorney, Agent, or Firm* — Lucas & Mercanti, LLP; Peter J. Phillips

(57) ABSTRACT

An apparatus to produce an OCT of an eye or a brain of a patient to identify one or more plaques in a plurality of discrete OCT retinal layers. The apparatus also includes a plurality of methods for identifying one or more plaques in a plurality of discrete OCT retinal layers that can include a contrast agent and a normative database.

14 Claims, 5 Drawing Sheets

(56) References Cited

OTHER PUBLICATIONS

Anderson et al., Characterization of b amyloid assemblies in drusen: the deposits associated with aging and age-related macular degeneration. Experimental Eye Research 78 (2004) 243-256.*

Yi et al., Spectral domain optical coherence tomography for quantitative evaluation of drusen and associated structural changes in non-neovascular age-related macular degeneration. Br J Ophthalmol 2009;93:176-181.*

Rosen et al., Simultaneous OCT/SLO/ICG Imaging. Investigative Ophthalmology & Visual Science, Feb. 2009, vol. 50, No. 2, 851-860.*

Koronyo-Hamaoui et al., Identification of amyloid plaques in retinas from Alzheimer's patients and noninvasive in vivo optical imaging of retinal plaques in a mouse model. NeuroImage 54 (2011) S204-S217.*

Thal et al., UV light-induced autofluorescence of full-length Abeta-protein deposits in the human brain. Clin Neuropathal, Jan.-Feb. 2002;21(1);35-40*

\* cited by examiner

APPARATUS AND METHOD FOR IDENTIFYING ONE OR MORE AMYLOID BETA PLAQUES IN A PLURALITY OF DISCRETE OCT RETINAL LAYERS

This application claims priority to U.S. Provisional Application 61/468,818 filed on Mar. 29, 2011, the entire disclosure of which is incorporated by reference.

TECHNICAL FIELD & BACKGROUND

Imaging of amyloid-beta plaques (including amyloid, amyloid-beta peptides) and other pathology and anatomical features in the retina or brain is often unobtainable without the use of specialized contrast agents typically used in PET scan procedures. Imaging of amyloid-beta plaques (including amyloid in other forms such as amyloid peptides) located in the retina/ocular fundus at large are not visible with any retinal imaging modalities with the sole exception of curcumin reflectance and/or fluorescence imaging (and other contrast agents), and has been performed in vivo only in animals but not in live humans.

The present invention can be utilized in an OCT system that utilizes optical coherence tomography (OCT), analysis of deposits in discrete layers of OCT, and/or multispectral/hyperspectral imaging in combination with proprietary spectral wavelength selection, spectral analysis, and image processing and/or in combination with contrast agents such as curcumin to identify amyloid in the retina rendering it visible to the clinician.

The present invention differs from other medical imaging apparatuses in that traditional OCT and current fundus imaging techniques do not afford for the visualization of amyloid in the retina. The present invention solves this problem through a combination of optical technology in combination with spectral analysis, retinal layer segmentation and image processing, and also can be utilized with the use of a contrast agent via analysis of fluorescence and/or reflectance. By operating OCT and multispectral imaging devices at specific wavelengths allows the spectral signature of amyloid-beta plaques to be obtained from the data set utilizing image processing, either with or without a contrast agent. Further segmentation can be performed via spectral analysis and/or OCT to determine location of deposits in the retina.

The present invention more specifically is an apparatus and method that can be utilized for identifying one or more plaques in a plurality of discrete OCT retinal layers.

BRIEF DESCRIPTION OF THE DRAWINGS

The present invention will be described by way of exemplary embodiments, but not limitations, illustrated in the accompanying drawing in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is used repeatedly. The phrase generally does not refer to the same embodiment, however, it may. The terms "comprising", "having" and "including" are synonymous, unless the context dictates otherwise.

Figure 1:
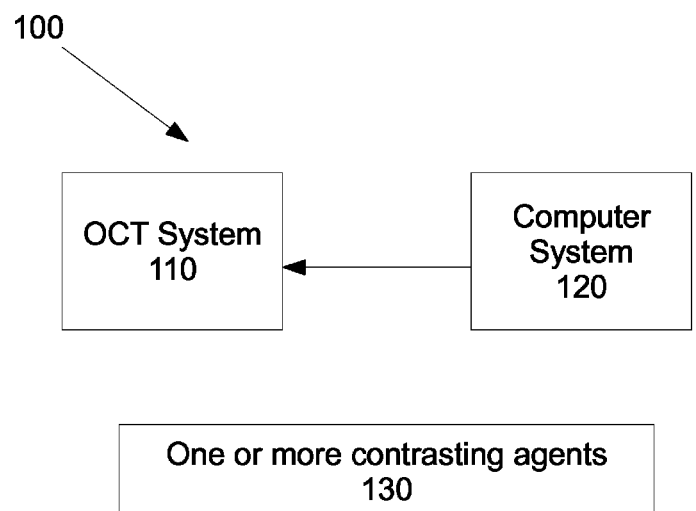
FIG. 1 illustrates a side perspective view of an apparatus for imaging an eye, in accordance with one embodiment of the present invention.

FIG. 1 illustrates an exploded perspective view of an apparatus 100 for producing an image of an eye, in accordance with one embodiment of the present invention. The image is an image of an amyloid-beta plaque, an amyloid or an amyloid-beta peptide or other pathology or anatomical features in the eye or brain of a user. The image is an amyloid-beta containing drusen image, an amyloid image or an amyloid-beta peptide image that resides within the discrete OCT retinal layers. The apparatus 100 detects the amyloid-beta plaque, the amyloid or the amyloid-beta peptide by a spectral signature. The apparatus 100 also performs a maximum and minimum intensity projection (MIP/MinIP). The apparatus 100 specifically can be utilized for identifying one or more amyloid beta plaques and amyloid containing drusen in a plurality of discrete OCT retinal layers.

The apparatus 100 for producing an image of an eye includes an OCT system 110 and a computer system 120. The OCT system 110 produces the image of an eye of a patient and can be any suitable OCT system 110. The computer system 120 processes data and controls the apparatus 100 that is in communication with the OCT system 110. The computer system 120 can be any suitable computer system 120 that can be used in combination with the apparatus 100. The personal computer 120 forms the center of the apparatus 100 and processes data and controls the OCT system 110. The personal computer 120 is a relatively compact computer, embedded computer, or tablet computer of relatively high processing power using a standardized operating system.

The apparatus 100 is utilized in combination with one or more contrast agents 130. The one or more contrast agents 130 is one or more selected from the group consisting of curcumin, one or more curcumin derivatives, Thioflavin S, one or more Thioflavin derivatives, Thioflavin T, one or more Thioflavin T derivatives, Congo Red, one or more Congo Red derivatives, methoxy-X04, Pittsburgh CompoundB (PiB), DDNP or Chrysamine-G.

The apparatus 100 produces an image that is an amyloid-beta plaque image, an amyloid image or an amyloid-beta peptide image that resides within the discrete OCT retinal layers. The apparatus 100 generates the amyloid-beta plaque image, the amyloid image or the amyloid-beta peptide image by a spectral signature. The apparatus 100 also performs a maximum and minimum intensity projection to define a volume of interest (VOI) of a specific region of interest and one or more discrete retinal layers.

The apparatus 100 is utilized for identifying one or more plaques in a plurality of discrete OCT retinal layers. The apparatus 100 includes evaluating one or more locations of plaques in the discreet locations of the discrete OCT retinal layers.

In one embodiment of the present invention, identification of the specific spectral wavelength and signature is identified with amyloid in the retina and brain possibly in combination with image subtraction techniques and other image processing techniques to isolate amyloid, and/or in combination with OCT to determine location of deposits in the retina.

In one embodiment of the present invention, the OCT data is presented with traditional OCT display modalities and/or en face so as to render familiar retinal images. In another embodiment of the present invention, the data is compared against a normative database and a plaque load is determined indicating a relative severity of the disease state.

In one embodiment of the present invention, OCT is performed using specific wavelengths that allow for the visualization of amyloid, and/or amyloid containing deposits in the retina and brain, with or without contrast agents. OCT data sets are obtained and analysis is performed to identify spectral signature and location aspects of amyloid in the retinal layers. These spectral components that correspond to amyloid are subsequently displayed in the OCT data set including en face presentation and/or in combination with traditional retinal imaging modalities. Spectral signal characteristics can be combined with other specific spectral components to render traditional OCT data sets in combination with an amyloid spectral data set.

In another embodiment of the present invention, a minimum threshold technique in combination with an adaptive spectral windowing technique is applied to the one or more data sets to render visualization of previous unseen features in OCT (and/or other imaging modality such as Autofluorescence) data sets. In another embodiment of the present invention, this technique is applied to not only amyloid but also other pathology and also anatomical features of the retina, with or without contrast agents, analyzing fluorescence and/or reflectance.

In another embodiment of the present invention, the OCT system, or traditional optical imaging device (hyper, multispectral, Autofluorescence, etc.) is operated at multiple/specific spectral wavelengths to tease out desired signature and information from amyloid and other pathology/retinal features.

In another embodiment of the present invention, curcumin (which binds to amyloid) is used as a contrast agent in combination with OCT to discreetly identify amyloid in specific retinal layers.

In another embodiment of the present invention, optical and OCT methods are used in combination with curcumin to identify amyloid by spectral signature, at a location in the retina, or a combination with another contrast agent.

Another embodiment of the present invention utilizes a fluorescent marker selected from the group including but not limited to curcumin, curcumin derivatives, Thioflavin S, Thioflavin derivatives, Thioflavin T, Thioflavin derivatives, Congo Red, Congo Red derivatives, methoxy-X04, Pittsburgh CompoundB (PiB), DDNP, Chrysamine-G, and combinations thereof. Imaging the contrast agents can be performed with traditional optical imaging, and/or multi and hyperspectral/Autofluorescence, and/or OCT or exclusively with OCT or any of the previously mentioned modalities individually.

Another embodiment of the present invention utilizes an OCT system that is used in combination with one or more components including a spectrometer, a fluorescence microscope, a stereomicroscope, a mercury arc lamp, a variable wavelength light source, a xenon arc lamp, an LED source, a tunable light source or a swept source, a CCD gated camera, a color digital camera, an acoustic-optic tunable filter based spectral image acquisition system, one or more confocal imaging devices, one or more scanning laser ophthalmoscope devices, a plurality of adaptive optics, an imaging software module, and/or any combinations thereof.

Another embodiment of the present invention utilizes a plurality of modalities including OCT, multispectral imaging, hyperspectral imaging, Autofluorescence, retinal angiography, one or more confocal retinal imaging devices, one or more systems utilized in combination with one or more components that include a spectrometer, a fluorescence microscope, a stereomicroscope, a mercury arc lamp, a variable wavelength light source, a xenon arc lamp, an LED source, a tunable light source or a swept source, a CCD or a CMOS gated camera, a color digital camera, an acoustic-optic tunable filter-based spectral image acquisition system, one or more confocal imaging devices, one or more scanning laser ophthalmoscope devices, adaptive optics, imaging software, and/or any combinations thereof. These modalities perform a Maximum/Minimum Intensity Projection (MIP/MiniP) and/or in combination with other specific one or more discreet spectral signatures on OCT and/or in combination with any of the above modalities, with or without contrast or angiographic agents. These contrast agents include but are not limited to curcumin, fluorescein, and ICG, for the identification of amyloid in the retina. Maximum intensity projection (MIP) and minimum intensity projection (MiniP) are volume-rendering techniques in which suitable editing methods are used to define the volume of interest (VOI). All of the image data set may be used, or the volume may be confined to a region of interest (ROI).

In one embodiment of the present invention, only desired features are included or excluded from VOI. The actual images are generated by projecting the volume of interest onto a viewing plane and displaying the maximum OCT (and/or other imaging modalities) scan numbers (for MIP) or the minimum OCT (and/or other imaging modalities) numbers (for MiniP) that are encountered along the direction of the projection. This technique ensures that optimum contrast is produced between small, high contrast structures and surrounding tissues.

In another embodiment of the present invention, an apparatus specifically can be utilized for identifying one or more plaques in a plurality of discrete OCT retinal layers.

In another embodiment of the present invention, a method specifically can be utilized for identifying one or more plaques in a plurality of discreet OCT retinal layers.

Figure 2:
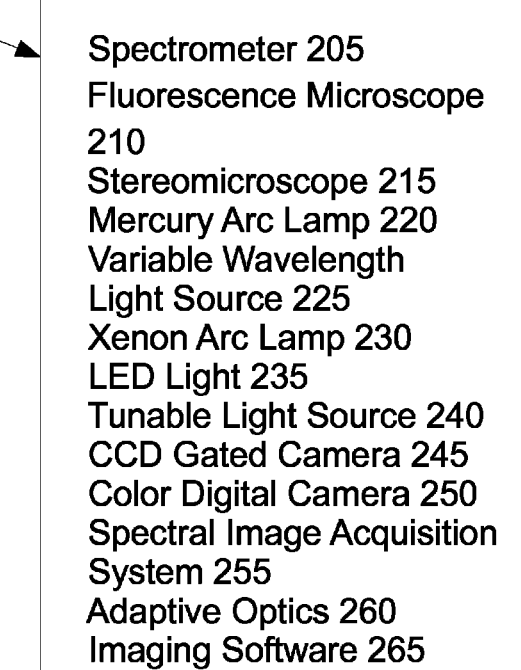
FIG. 2 is a block diagram of various components that can be utilized in combination with an apparatus for imaging an eye, in accordance with one embodiment of the present invention.

FIG. 2 is a block diagram of a plurality of various components 200 that can be utilized in combination with an apparatus for imaging an eye, in accordance with one embodiment of the present invention.

These components 200 are selected from the group consisting of a spectrometer 205, a fluorescence microscope 210, a stereomicroscope 215, a mercury arc lamp 220, a variable wavelength light source 225, a xenon arc lamp 230, an LED light 235, a tunable light source or a swept source 240, a CCD gated camera 245, a color digital camera 250, an acoustic-optic tunable filter-based spectral image acquisition system 255, a plurality of adaptive optics 260, imaging software 265 and any combinations thereof.

Figure 3:
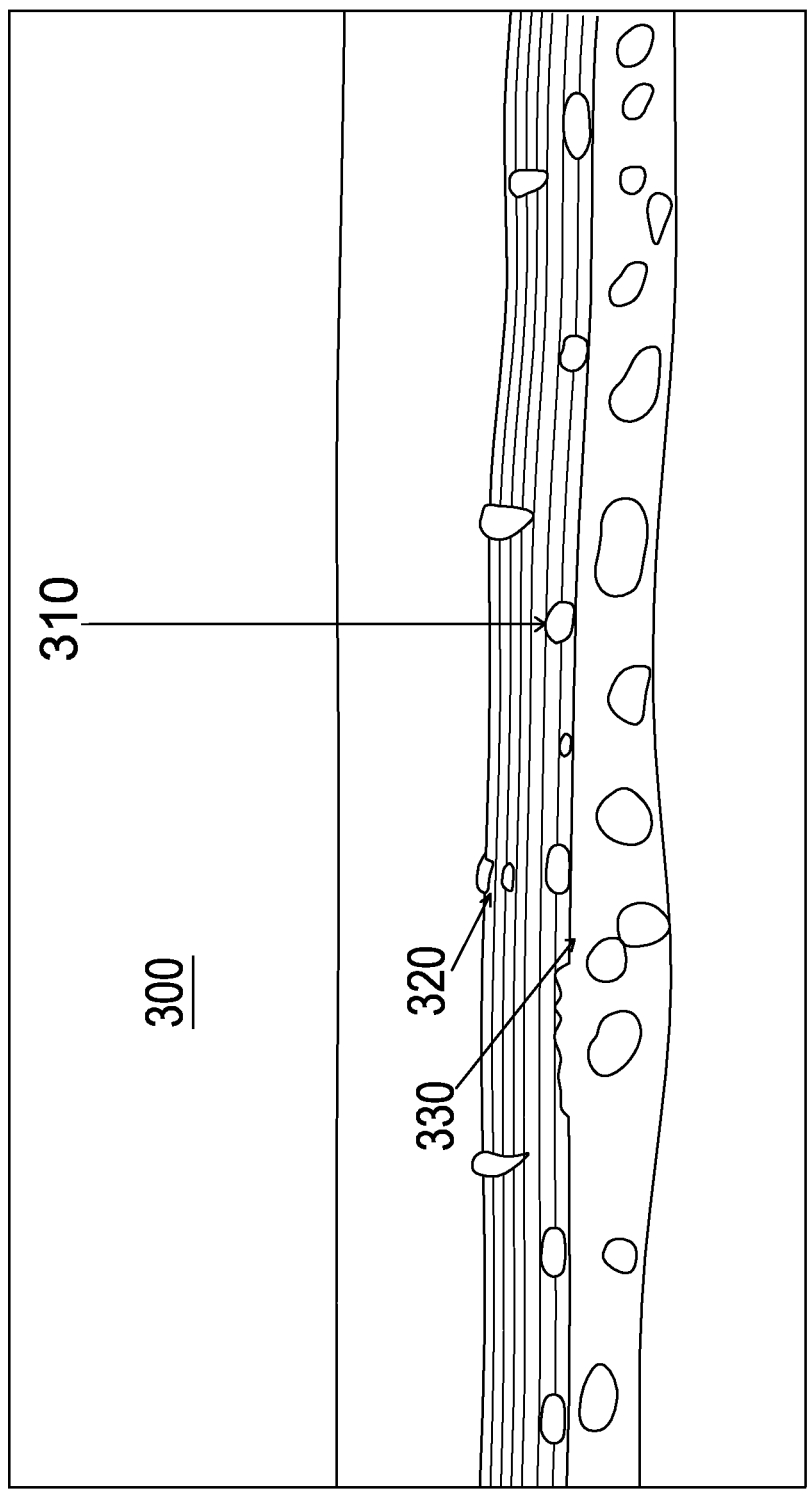
FIG. 3 illustrates a photographic image of one or more plaques in a plurality of discrete OCT retinal layers, in accordance with one embodiment of the present invention.

FIG. 3 illustrates a photographic image 300 of one or more plaques in a plurality of discrete OCT retinal layers, in accordance with one embodiment of the present invention.

The photographic image 300 includes one or more plaques 310, a plurality of discrete OCT retinal layers 320 and a retinal pigment epithelium 330. The one or more plaques 310 are identified utilizing the methods described in FIGS. 4 and 5 and are designed to identify the one or more plaques 310. The one or more plaques 310 are identified utilizing the apparatuses in FIG. 1 and FIG. 2. The discrete OCT retinal layers 320 are at specific locations where the one or more plaques 310 reside. The retinal pigment epithelium 330 is included in FIG. 3 and the one or more plaques 310 are located above the retinal pigment epithelium 330 as illustrated in FIG. 3.

Figure 4:
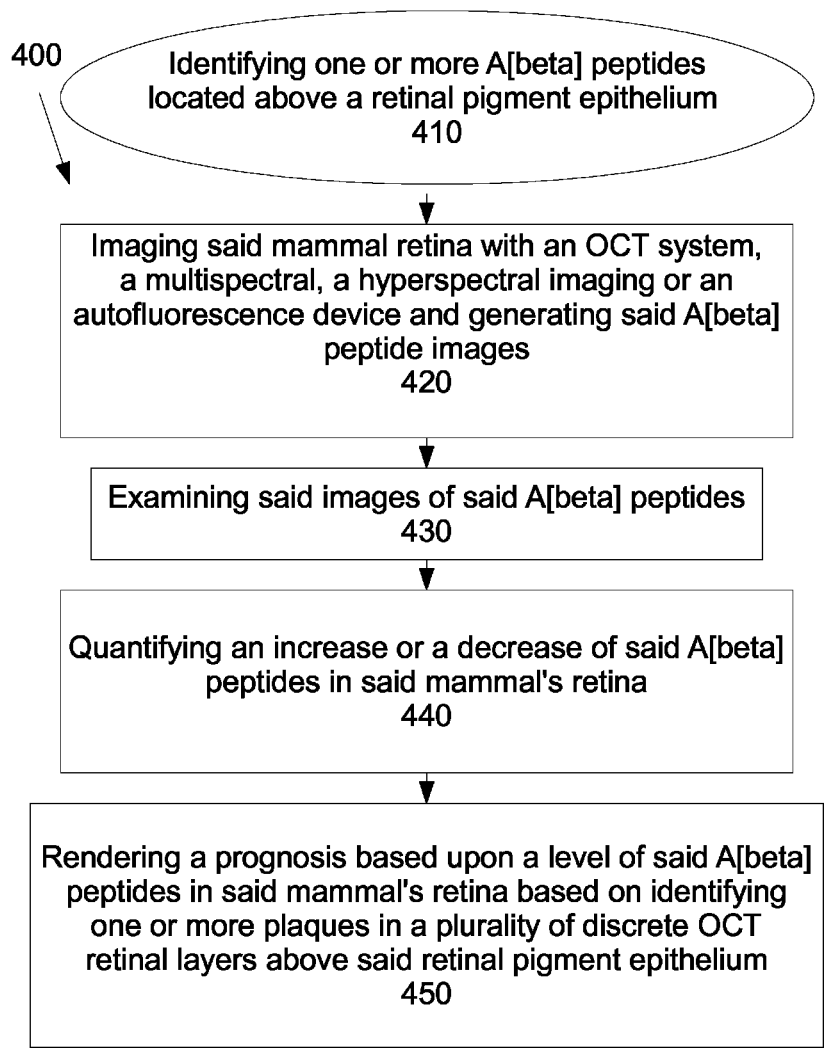
FIG. 4 illustrates a flowchart of a method for identifying one or more plaques in a plurality of discrete OCT retinal layers, in accordance with one embodiment of the present invention.

FIG. 4 illustrates a flowchart of a method 400 for identifying one or more amyloid beta plaques and amyloid containing drusen in a plurality of discrete OCT retinal layers, in accordance with one embodiment of the present invention. The method 400 includes the steps of identifying one or more A(beta) peptides located above a retinal pigment epithelium thereby differentiating the one or more A(beta) peptides from drusen 410, imaging the mammal's retina with an OCT system, a multispectral, a hyperspectral imaging or an Autofluorescence imaging device and generating the A(beta) peptide images 420, examining the images of the A(beta) peptides 430 (with or without the use of contrast agents), quantifying an increase or a decrease of the A(beta) peptides in the mammal's retina 440 and rendering a prognosis based upon a level of the A(beta) peptides in the mammal's retina based on identifying one or more plaques in a plurality of discrete OCT retinal layers above the retinal pigment epithelium 450. The step of identifying one or more A(beta) peptides 410 is performed by the plurality of apparatuses previously described and outlined in FIGS. 1 and 2. The step of imaging the mammal's retina with an OCT system, a multispectral, a hyperspectral imaging or an Autofluorescence imaging device 420 detects possible amyloid in a mammal's retina and brain. The step of examining the images of the A(beta) peptides 430 is performed typically by the computer system 120 previously described in FIG. 1, although other suitable methods and systems can also be used. The step of quantifying an increase or decrease of the A(beta) peptides in the subject's retina 440 is done typically in comparison to a prior diagnosis and can be compared to any suitable previous diagnosis performed typically by the computer system 120 previously described in FIG. 1, although other suitable methods and systems can also be used. The step of 5 rendering a prognosis based upon a level of the A(beta) peptides in the mammal's retina based on identifying one or more plaques in a plurality of discrete OCT retinal layers 450 includes evaluating one or more locations of plaques in the discreet locations of the discrete OCT retinal layers. The method 400 imaging step 410 includes imaging a mammal's retina with the OCT system, the multispectral, the hyperspectral imaging or the Autofluorescence imaging device to detect possible amyloid in the mammal's retina and brain. The method 400 rendering step 450 includes evaluating one or more discrete locations of the one or more plaques in the one or more discreet locations of the one or more retinal layers, above the retinal pigment epithelium as differentiated from the drusen which reside in or below the retinal pigment epithelium.

Figure 5:
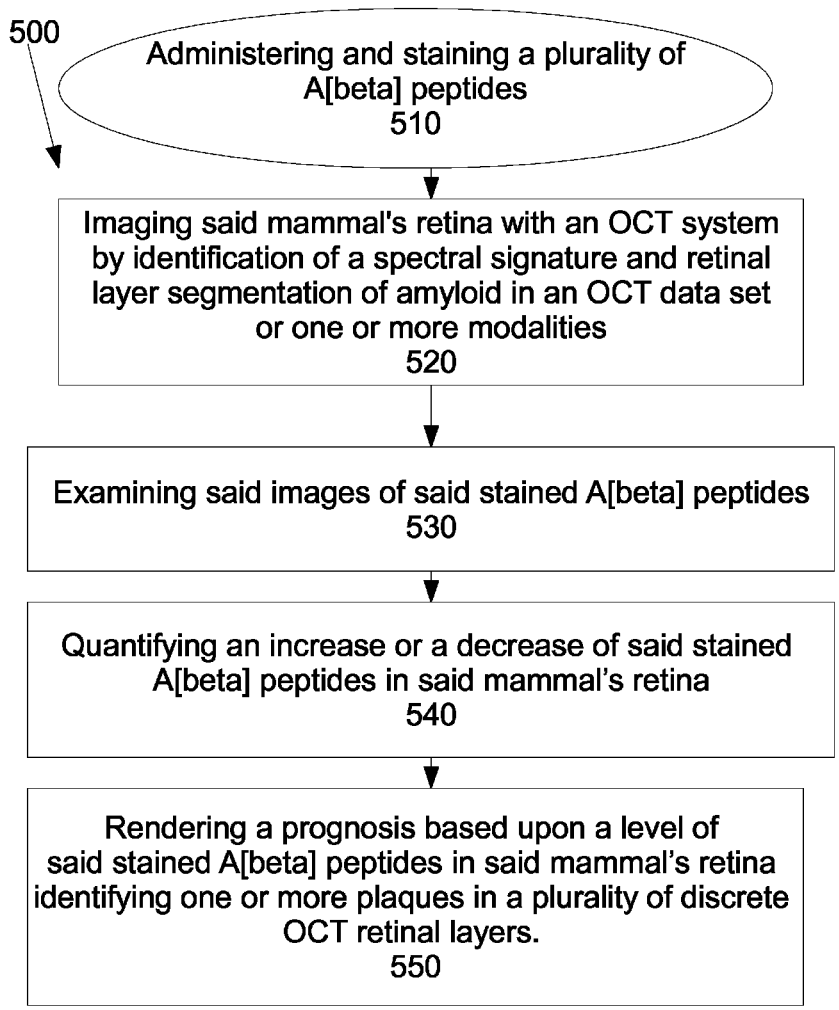
FIG. 5 illustrates a flowchart of a method for identifying one or more plaques in a plurality of discrete OCT retinal layers with a contrast agent and a normative database, in accordance with one embodiment of the present invention.

FIG. 5 illustrates a flowchart of a method 500 for identifying one or more amyloid beta plaques and amyloid containing drusen in a plurality of discrete OCT retinal layers with a contrast agent and a normative database, in accordance with one embodiment of the present invention. The method 500 steps include administering and staining a plurality of A(beta) peptides 510, imaging the mammal's retina with an OCT system by identification of a spectral signature and retinal layer segmentation of amyloid in an OCT data set or one or more other modalities 520, wherein the modalities include varying one or more wavelengths of the OCT system and analyzing a generated signal to derive an amyloid signal. Additional steps of the method 500 include examining the images of the stained A(beta) peptides 530, quantifying an 5 increase or a decrease of stained A(beta) peptides in the mammal's retina 540 and rendering a prognosis based upon a level of the stained A(beta) peptides in the mammal's retina identifying one or more plaques in a plurality of discrete OCT retinal layers 550. The OCT data set can be compared to other OCT data sets in a normative database residing in the computerized system. The step of rendering a prognosis based upon the level of the stained A(beta) peptides in the mammal's retina 550 also includes evaluating one or more locations of plaques in the discreet locations of the discrete OCT retinal layers. The method 500 modalities include varying one or more wavelengths of the OCT system and analyzing a generated signal to derive an amyloid signal. The method 500 signals are generated with the OCT system and a multispectral confocal and one or more optical imaging techniques. The signals can be generated with one or more image and OCT layer segmentation techniques. The signals can be generated from the one or more optical imaging techniques exclusively using the one or more wavelengths. The signals can be generated from an exclusive OCT identification of deposit and layer segmentation. The signals can be generated from an exclusive hyperspectral imaging, from exclusive multispectral imaging and from autofluorescence.

The spectral signature of the amyloid is obtained by spectral analysis and image processing and the amyloid is generated with the contrast agent to be analyzed. The contrast agent is one or more selected from the group consisting of curcumin, one or more curcumin derivatives, Thioflavin S, one or more Thioflavin derivatives, Thioflavin T, one or more Thioflavin T derivatives, Congo Red, one or more Congo Red derivatives, methoxy-X04, Pittsburgh CompoundB (PiB), DDNP or Chrysamine-G. The OCT data set is compared to one or more other OCT data sets in the normative database and a subsequent disease state and a subsequent normal state is determined based on a comparison of the normative database and a location within the retina compared with one or more other disease states.

While the present invention has been related in terms of the foregoing embodiments, those skilled in the art will recognize that the invention is not limited to the embodi-

What is claimed is:

1. A system to produce an image of an eye of a patient to identify at least one amyloid beta plaque and amyloid containing drusen in a plurality of discrete retinal layers, comprising:
   an (optical coherence tomography) OCT system for obtaining an amyloid beta plaque image, an amyloid image or an amyloid beta peptide image that resides within said discrete retinal layers having a spectral signature;
   a computer system that processes data and controls said apparatus that is in communication with said OCT system, wherein said computer system is a compact computer;
   at least one contrast agent, selected from the group consisting of curcumin, curcumin derivatives, Thioflavin S, Thioflavin derivatives, Thioflavin T, Thioflavin T derivatives, Congo Red, one or more Congo Red derivatives, methoxy-X04, Pittsburgh Compound S (PiB), DDNP and Chrysamine-G;
   wherein said system includes at least one component selected from the group consisting of a mercury arc lamp, a variable wavelength light source, a xenon arc lamp, an LED light source, a tunable light source or swept source, and an acoustic-optic tunable filter-based spectral image acquisition system
   wherein said apparatus performs a maximum and a minimum intensity projection to define a volume of interest of a specific region of interest and said discrete retinal layers, to obtain different images of plaque and drusen to thereby provide plaque and drusen differentiation.

2. A method for identifying one or more amyloid beta plaques and amyloid containing drusen in a plurality of discrete OCT retinal layers, comprising the steps of:
   identifying one or more A(beta) peptides located above a retinal pigment epithelium thereby differentiating said one or more A(beta) peptides from said drusen;
   imaging a mammal's retina with an OCT system and a multispectral and a hyperspectral imaging or an Autofluorescence imaging device;
   examining said images of said A(beta) peptides; and
   quantifying an increase or a decrease of said A(beta) peptides in said mammal's retina.

3. The method according to claim 2, further comprising evaluating one or more discrete locations of said one or more plaques in said one or more discreet locations of said one or more retinal layers, above said retinal pigment epithelium, as differentiated from said drusen which reside in or below said retinal pigment epithelium.

4. A method for staining one or more amyloid beta plaques and amyloid containing drusen in a plurality of discrete OCT retinal layers with a normative database, comprising the steps of:
   administering and staining a plurality of A(beta) peptides with a contrasting agent;
   imaging said mammal's retina with an OCT system by identification of a spectral signature and retinal layer segmentation of amyloid in an OCT data set or one or more modalities;
   examining said images of said stained A(beta) peptides;
   quantifying an increase or a decrease of said stained A(beta) peptides in said mammal's retina.

5. The method according to claim 4, wherein said one or more modalities include varying one or more wavelengths of said OCT system and analyzing a generated signal to derive an amyloid signal.

6. The method according to claim 4, wherein said signals are generated with said OCT system and a multispectral confocal and one or more optical imaging techniques.

7. The method according to claim 4, wherein said signals are generated with one or more image and OCT layer segmentation techniques.

8. The method according to claim 4, wherein said signals are generated from said one or more optical imaging techniques exclusively using said one or more wavelengths.

9. The method according to claim 4, wherein said signals are generated from an exclusive OCT identification of deposit and layer segmentation.

10. The method according to claim 4, wherein said signals are generated from an exclusive hyperspectral imaging.

11. The method according to claim 4, wherein said signals are generated from exclusive multi-spectral imaging.

12. The method according to claim 4, wherein said signals are generated from autofluorescence.

13. The method according to claim 4, wherein said spectral signature of said amyloid is obtained by spectral analysis and image processing.

14. The method according to claim 4, wherein said OCT data set is compared to one or more other OCT data sets in said normative database and a subsequent disease state and a subsequent normal state is determined based on a comparison of said normative database and a location within said retina compared with one or more other disease states.

* * * * *